(12) United States Patent
Mürner et al.

(10) Patent No.: US 8,287,575 B2
(45) Date of Patent: Oct. 16, 2012

(54) POLYAXIAL LOCKING MECHANISM

(75) Inventors: Beat Mürner, Reichenbach (CH); Philippe Lehmann, Lamboing (CH)

(73) Assignee: Stryker Trauma GmbH (DE)

( * ) Notice: Subject to any disclaimer, the term of this patent is extended or adjusted under 35 U.S.C. 154(b) by 702 days.

(21) Appl. No.: 11/595,795

(22) Filed: Nov. 9, 2006

(65) Prior Publication Data

US 2008/0114359 A1    May 15, 2008

(51) Int. Cl.
| A61B 17/56 | (2006.01) |
| A61B 17/58 | (2006.01) |
| A61B 17/80 | (2006.01) |
| A61B 17/04 | (2006.01) |
| A61B 17/86 | (2006.01) |
| A61F 2/30 | (2006.01) |
| A61F 2/08 | (2006.01) |

(52) U.S. Cl. ............ 606/287; 606/303; 606/319; 606/71
(58) Field of Classification Search .............. 606/71, 606/86 B, 286, 287, 303, 319
See application file for complete search history.

(56) References Cited

U.S. PATENT DOCUMENTS

| 5,053,036 A | 10/1991 | Perren et al. |
| 5,531,554 A | 7/1996 | Jeanson et al. |
| 5,904,683 A * | 5/1999 | Pohndorf et al. ............ 606/287 |
| 5,954,722 A | 9/1999 | Bono |
| 6,193,721 B1 | 2/2001 | Michelson |
| 6,235,003 B1 | 5/2001 | Dysarz |
| 6,235,033 B1 | 5/2001 | Brace et al. |
| 6,454,771 B1 | 9/2002 | Michelson |
| 6,572,622 B1 | 6/2003 | Schafer et al. |
| 6,575,975 B2 | 6/2003 | Brace et al. |
| 6,730,091 B1 | 5/2004 | Pfefferle et al. |
| 6,780,186 B2 * | 8/2004 | Errico et al. ................. 606/71 |
| 6,916,323 B2 * | 7/2005 | Kitchens .................. 606/86 R |
| 7,229,443 B2 | 6/2007 | Eberlein et al. |

(Continued)

FOREIGN PATENT DOCUMENTS

CA    2 471 843 A1    7/2003
(Continued)

OTHER PUBLICATIONS

U.S. Appl. No. 10/999,132, filed Nov. 2004.

Primary Examiner — Kevin T Truong
Assistant Examiner — David Bates
(74) Attorney, Agent, or Firm — Lerner, David, Littenberg, Krumholz & Mentlik, LLP

(57) ABSTRACT

An improved polyaxial mechanism is disclosed. The mechanism preferably works in conjunction with a bone plate and fixation mechanism, such as a screw, rod, or the like. The improved polyaxial mechanism increases the strength of the locking among the locking mechanism, fixation mechanism, and bone plate. In addition, the improved polyaxial mechanism allows for easy locking among the elements, as well as more difficulty in unlocking the elements. A method for utilizing the improved polyaxial mechanism is also disclosed.

30 Claims, 10 Drawing Sheets

U.S. PATENT DOCUMENTS

| | | |
|---|---|---|
| 7,273,481 B2 * | 9/2007 | Lombardo et al. .......... 606/86 A |
| 7,303,564 B2 | 12/2007 | Freid et al. |
| 7,758,620 B2 * | 7/2010 | Porcher ........................ 606/290 |
| 2001/0037112 A1 * | 11/2001 | Brace et al. ..................... 606/69 |
| 2003/0187440 A1 | 10/2003 | Richelsoph et al. |
| 2003/0187442 A1 | 10/2003 | Richelsoph et al. |
| 2004/0127896 A1 * | 7/2004 | Lombardo et al. .............. 606/61 |
| 2005/0010219 A1 * | 1/2005 | Dalton ............................ 606/61 |
| 2005/0043736 A1 * | 2/2005 | Mathieu et al. ................. 606/73 |
| 2005/0143742 A1 | 6/2005 | Porcher |
| 2005/0228386 A1 | 10/2005 | Ziolo et al. |
| 2006/0058797 A1 * | 3/2006 | Mathieu et al. ................. 606/69 |
| 2006/0149251 A1 * | 7/2006 | Ziolo et al. ..................... 606/69 |
| 2006/0149256 A1 * | 7/2006 | Wagner et al. ................. 606/69 |
| 2006/0190090 A1 | 8/2006 | Plaskon |
| 2007/0123879 A1 | 5/2007 | Songer et al. |

FOREIGN PATENT DOCUMENTS

| | | |
|---|---|---|
| DE | 100 39 767 A1 | 7/2001 |
| FR | 2 674 118 A1 | 9/1992 |
| FR | 2 739 151 A1 | 3/1997 |
| FR | 2 744 011 A1 | 8/1997 |
| FR | 2 790 198 A1 | 9/2000 |
| FR | 2 844 702 | 3/2004 |
| WO | 94-07040 | 3/1994 |
| WO | 99/59492 A1 | 11/1999 |
| WO | 2004/071276 A2 | 8/2004 |
| WO | 2004/086990 A1 | 10/2004 |

* cited by examiner

POLYAXIAL LOCKING MECHANISM

BACKGROUND OF THE INVENTION

Screw-and-plate osteosynthesis systems must allow immobilizing of one or more bone fragments in reference to others. It is known to use spherical-head screws cooperating with a spherical aperture housed in a plate and bringing the plate into compression over the bone until the friction of the plate on the bone stabilizes the assembly. These assemblies allow choice of the angle of implantation of screws during the operation and causing a return movement and a compression of a detached bone fragment. Certain of these systems allow, due to the oblong shape of the aperture made in the plate, compression of one bone fragment on another. The shortcoming of these systems is their low resistance to compression stresses exerted parallel to the plane of the plate.

Use is also known of a second generation of screw-and-plate systems called monoaxial-locking and polyaxial-locking systems in which the strength of the assembly no longer depends on compression of the plate on the bone but on a fixation of the screw in the plate. These systems allow achieving assembly away from the bone with, for the more elaborate ones, the possibility of choosing the angle of implantation of screws during the operation while achieving strength sufficient for postoperative stresses.

Commonly owned U.S. Patent Publication No. 2005/0143742 ("the '742 publication"), the disclosure of which is hereby incorporated by reference herein, teaches an improvement to the above-noted and already useful devices. More particularly, the '742 publication teaches a device which is used for solidly connecting a part such as a plate to an underlying support (e.g., a bone) using at least one fixing element such as screw. According to the invention of the '742 publication, the fixing element takes the form of a threaded rod or screw which passes through a hole housing a ring belonging to the part, such that it is screwed into the support material. The ring is preferably a constriction ring including a non-circular outer profile which co-operates with the non-circular inner profile of the hole formed in the part. Upon rotation of the ring, such is wedged in place and constricted and thereby blocking the threaded rod or screw against movement with respect to the plate.

Even in view of the innovative and highly useful device taught in the '742 publication, which is itself an improvement upon well-known and useful technology, there still exists room for improved functionality and design in fixation of bone plates. For example, there exists a need for improved bending strength between the threaded rod or screw and the plate, among other improvements.

SUMMARY OF THE INVENTION

A first aspect of the present invention is a polyaxial locking mechanism for locking a fixation mechanism with respect to a bone plate. The polyaxial locking mechanism preferably includes a body disposed within an aperture formed in the bone plate. The body further includes a central opening for receiving the fixation mechanism, a slot formed through the body and into the central opening, and a circumferentially extending interior groove formed on an interior surface of the body. Preferably, in a loosened position, the body is capable of polyaxial movement with respect to the bone plate, and upon rotation of the body to a tightened position, the body, the fixation mechanism, and the bone plate are fixed with respect to one another.

A second aspect of the present invention is a polyaxial locking mechanism for locking a bone screw with respect to a bone plate. The polyaxial locking mechanism preferably includes a circular ring shaped body disposed within an aperture formed in the bone plate. The body further includes a central opening for receiving the bone screw, a slot formed through the body and into the central opening, a circumferentially extending interior groove formed on an interior surface of the body, and a plurality of exterior grooves formed on an exterior surface of the body, the exterior grooves being situated in different sections. Preferably, in a loosened position, the body is capable of polyaxial movement with respect to the bone plate, and upon rotation of the body to a tightened position, the body, the bone screw, and the bone plate are fixed with respect to one another.

A third aspect is a polyaxial locking mechanism for locking a bone screw with respect to a bone plate. The polyaxial locking mechanism preferably includes a circular ring shaped body disposed within an aperture formed in the bone plate. The body further includes a central opening for receiving the bone screw, a slot formed through the body and into the central opening, a circumferentially extending interior groove formed on an interior surface of the body, the interior groove adapted to engage a portion of the bone screw, a plurality of exterior grooves formed on an exterior surface of the body, the exterior grooves being situated in different sections, a cut out formed on the interior surface of the body, two peaks separated by a valley for use in engagement with a driver for rotating the body, and a circumferential wall for engagement with a head portion of the bone screw. Preferably, in a loosened position, the body is capable of polyaxial movement with respect to the bone plate, and upon rotation of the body to a tightened position, the body, the bone screw, and the bone plate are fixed with respect to one another.

A fourth aspect of the present invention is a fracture fixation system. In accordance with one embodiment of this fourth aspect, the fracture fixation system includes a bone plate having a non-circular aperture formed therein, a body disposed within the aperture, and a bone fastener received within the central opening of the body. The body preferably includes a central opening, a slot formed through the body and into the central opening, and a circumferentially extending interior groove formed on an interior surface of the body, the bone fastener having a head engaged with the circumferentially extending interior groove. Preferably, when in a loosened position, the body is capable of polyaxial movement with respect to the bone plate, and upon rotation of the body to a tightened position, the body, the bone fastener, and the bone plate are fixed with respect to one another.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
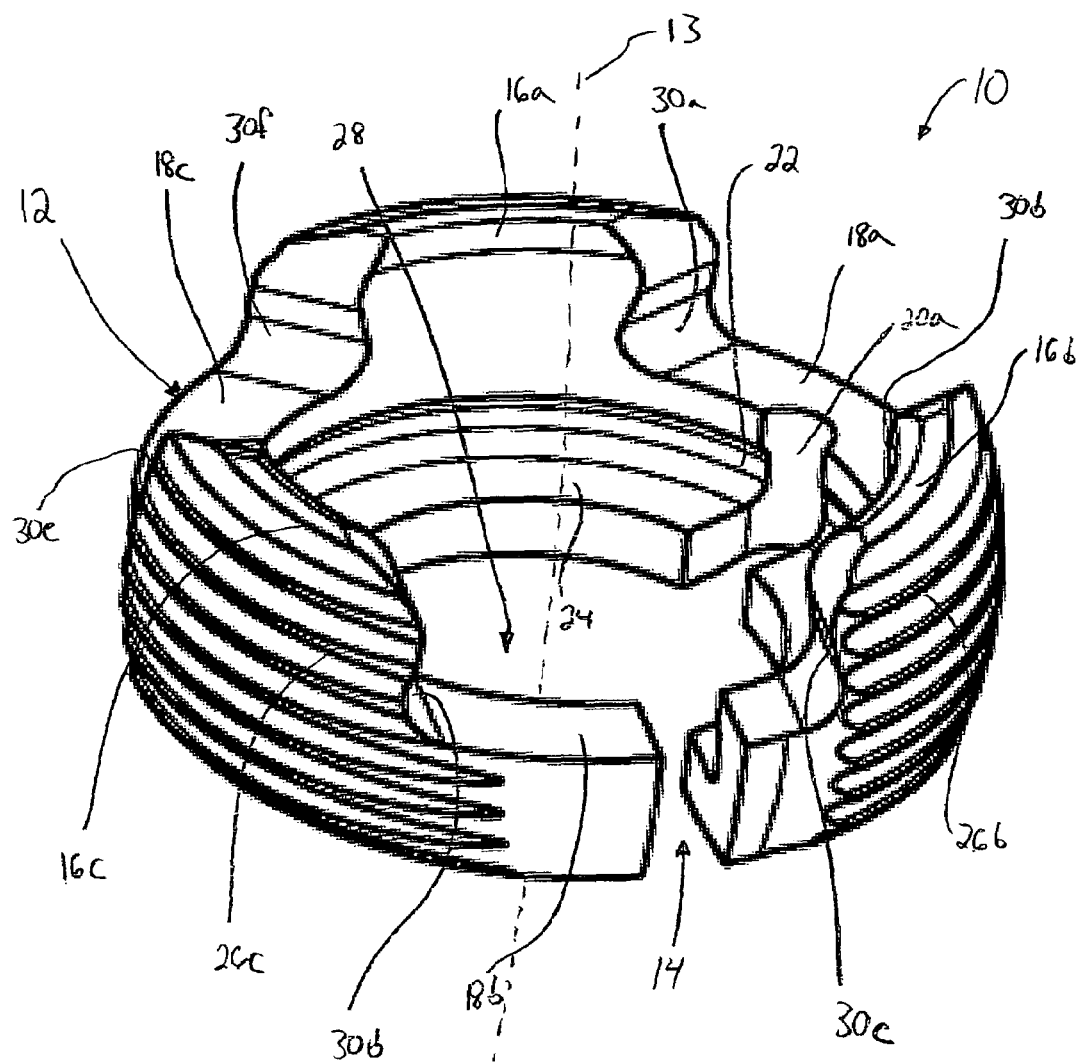
FIG. 1 is a perspective view of a polyaxial locking mechanism or ring in accordance with one embodiment of the present invention.

Referring to the drawings, wherein like reference numerals refer to like elements, there is shown in FIGS. 1-5, a polyaxial locking mechanism or ring designated generally by reference numeral 10. Ring 10 is preferably designed so as to be received within an aperture formed in a bone plate designed for use with the ring. This will be discussed more fully below. The figures depict a preferred embodiment ring 10. However, it is to be understood that ring 10 may vary in size and/or shaped depending upon the particular plate it is designed for. Likewise, differently configured rings fall within the scope of the present invention. For example, certain of the below discussed elements of ring 10 may vary according to the ultimate use of the ring within a particular patient.

Figure 2:
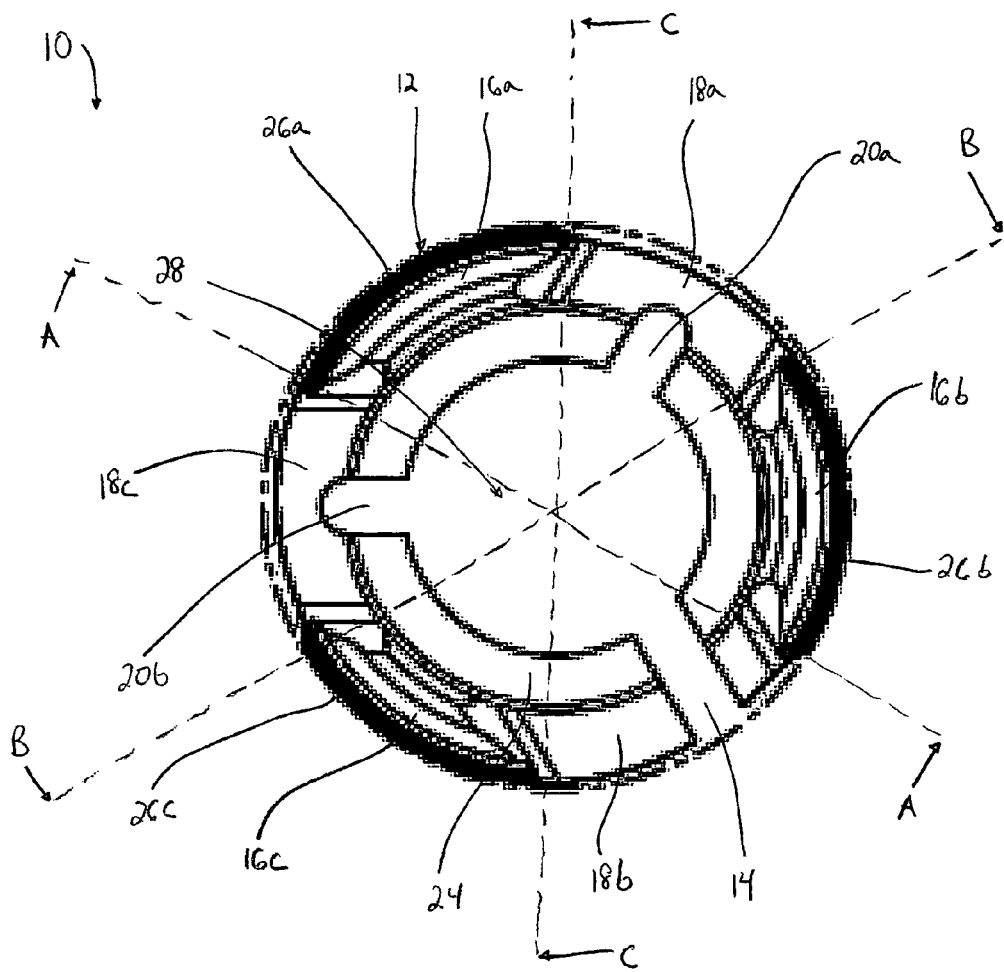
FIG. 2 is a top view of the polyaxial locking mechanism or ring shown in FIG. 1.
Figure 3:
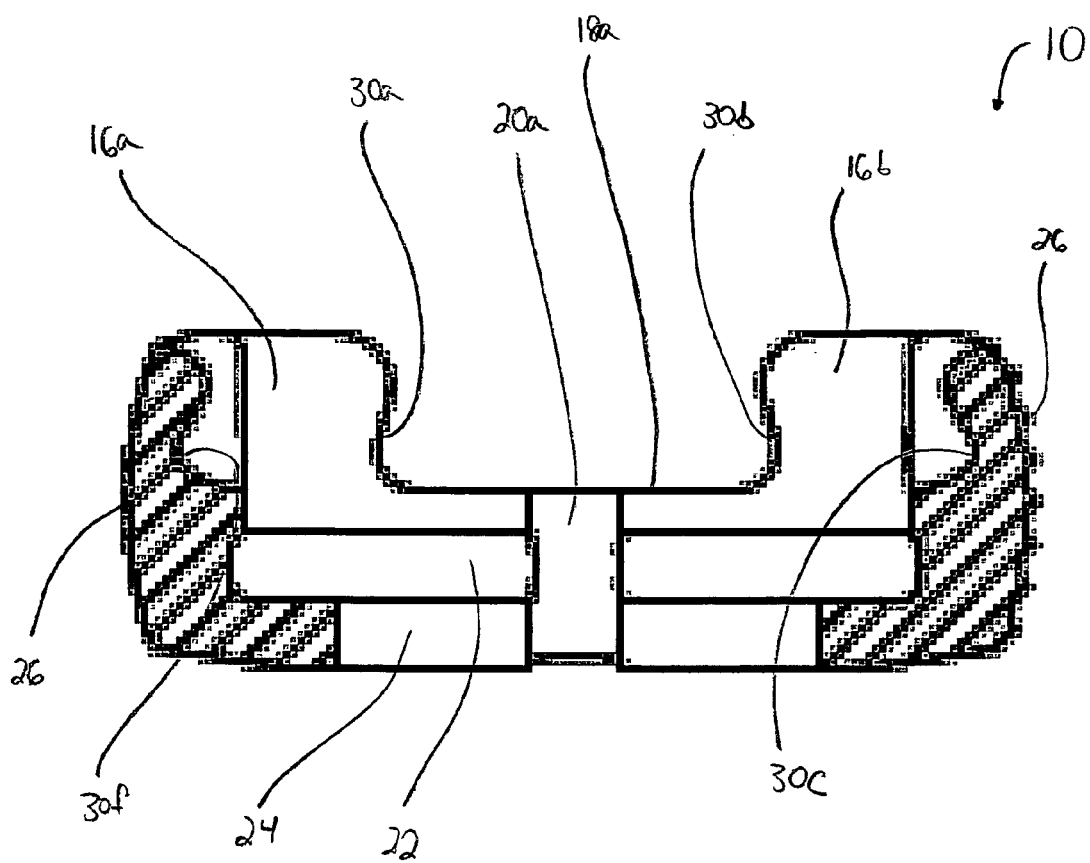
FIG. 3 is a cross sectional side view taken along line A-A of FIG. 2 of the polyaxial locking mechanism or ring shown in FIG. 1.
Figure 4:
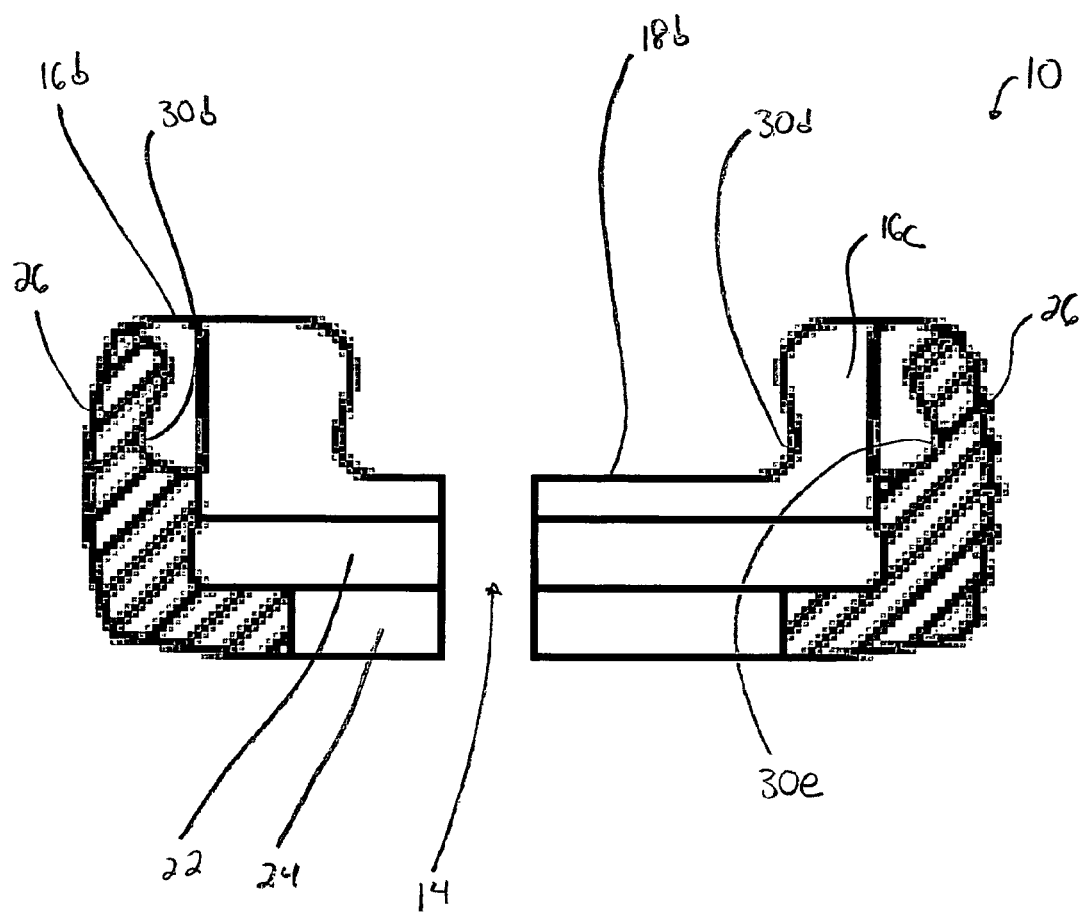
FIG. 4 is a cross sectional side view taken along line B-B of FIG. 2 of the polyaxial locking mechanism or ring shown in FIG. 1.
Figure 5:
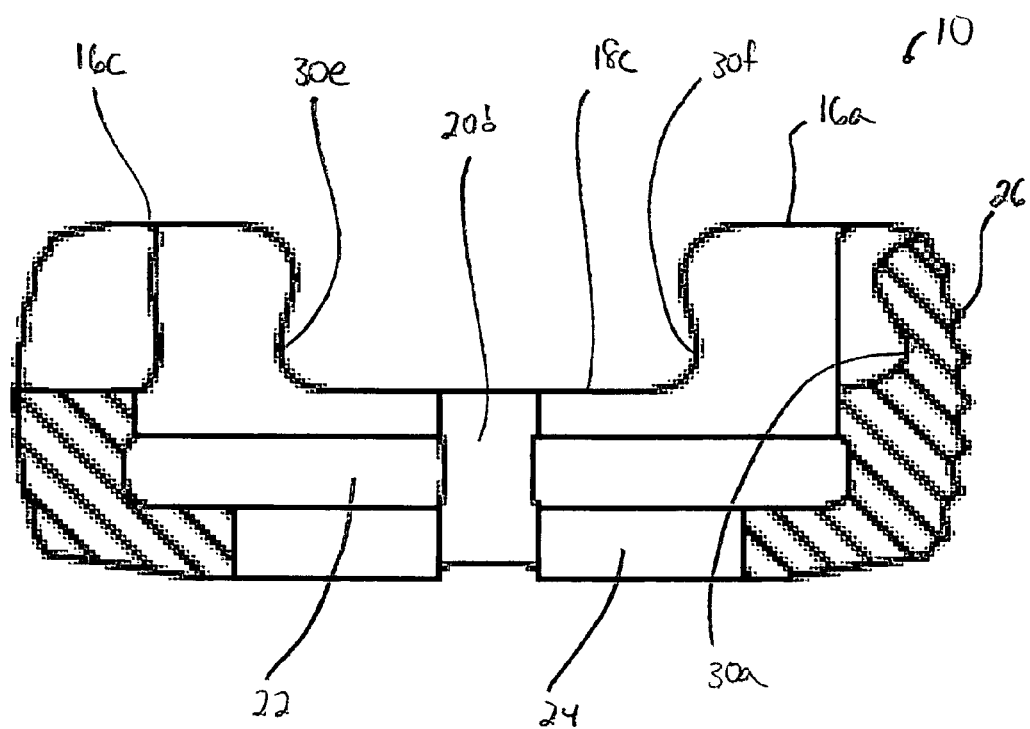
FIG. 5 is a cross sectional side view taken along line C-C of FIG. 2 of the polyaxial locking mechanism or ring shown in FIG. 1.

As is best shown in the perspective view of FIG. 1, ring 10 essentially consists of a body 12 which forms a ring-shape save for a slot 14. In the preferred embodiment, ring 10 is circular with a central axis 13. Body 12 includes several distinct elements and/or sections. More particularly, body 12 includes three peaks 16a-c separated by three valleys 18a-c, two cut outs 20a-b in the form of axial grooves (20b is best shown in FIG. 2), a circumferentially extending interior groove 22, a lower circumferential wall 24 and a plurality of exterior grooves separated into three distinct exterior grooved areas 26a-c. The ring shape of body 12 also forms a central opening 28 that is capable of receiving the head of a screw, a rod or other fixation mechanism. Furthermore, the cooperation between peaks 16a-c and adjacent valleys 18a-c forms tapered flanks 30a-f. The use of each of these elements will be discussed in detail below, as will their cooperation with other components in a bone plate system.

Figure 7:
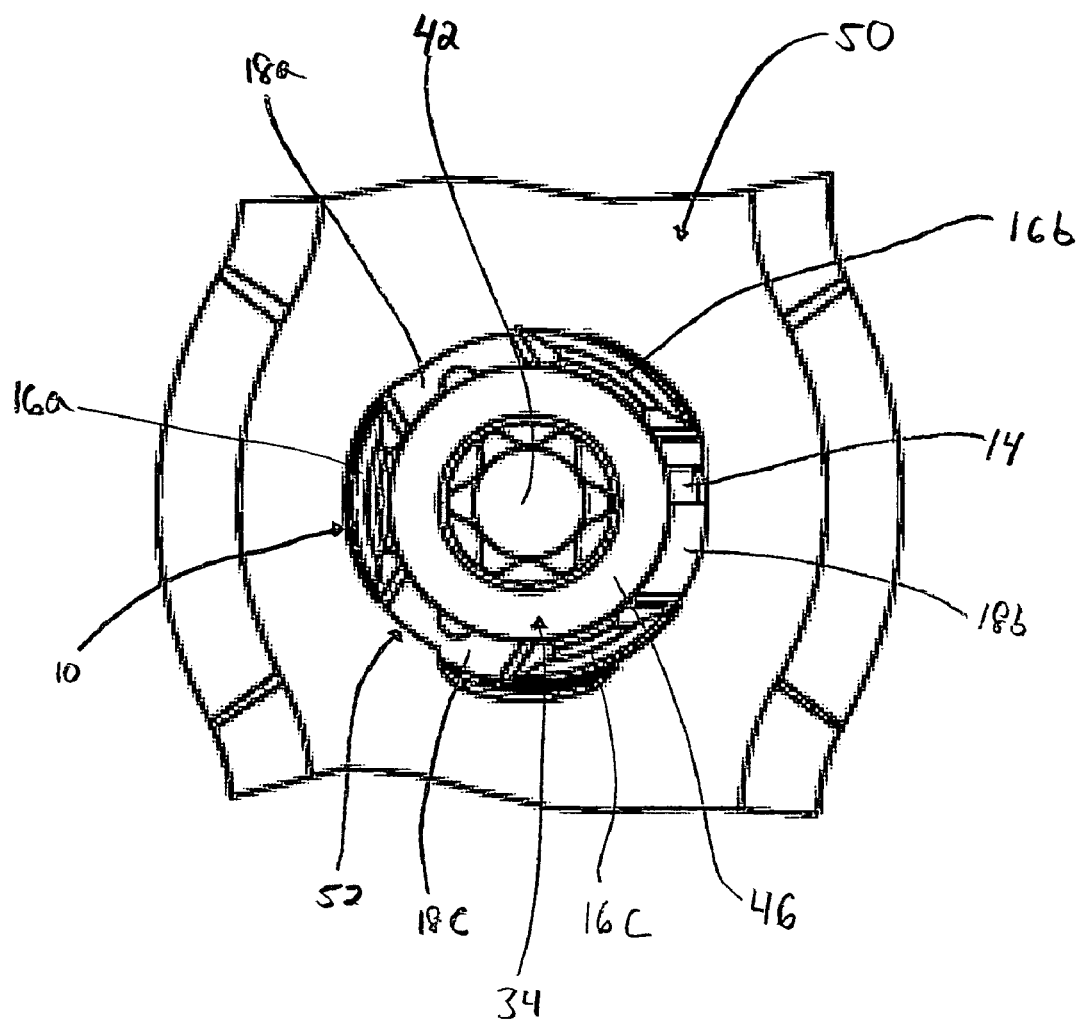
FIG. 7 is a top view of the polyaxial locking mechanism or ring of FIG. 1 in engagement with a screw and a bone plate.

As is mentioned above, ring 10 is designed so as to be received within an aperture 52 of a bone plate 50 (see the fully constructed top view of FIG. 7). The cooperation between ring 10 and aperture 52 is such that polyaxial movement of ring 10 is allowed, prior to tightening of the ring with respect to the plate. Initially, ring 10 is capable of rotating (to a certain extent) about several different axis with respect to aperture 52. Aperture 52 is preferably non-circular, such that a tightening rotation of ring 10 about an axis normal to aperture 52 (i.e., in the direction of central axis 13) causes constriction of ring 10. More particularly, rotation of ring 10 in this fashion causes a reduction in the size of slot 14 and central opening 28. This constriction thereby locks or retains ring 10 on the fastening element and in position with respect to plate 50 and also retains any screw, rod or other fixation mechanism disposed within central opening 28. It is to be understood that cut outs 20a and 20b are provided to weaken the overall structure of body 12 and therefore make the rotation and constriction of ring 10 easier. Because cut outs 20a and 20b are disposed on the interior of body 12 their inclusion essentially removes material in body 12 which thereby provides deflectable weakened wall areas which lessens the force provided by the structure against constriction. Thus, normal tightening rotation of ring 10 is preferably made much easier.

The aforementioned constriction capabilities of ring 10 require that body 12 be constructed of a material suitable for the movement required. In addition, ring 10 is preferably designed so that upon a loosening rotation of ring 10 with respect to plate 50, the constriction force is reduced or completely removed. Hence, body 12 of ring 10 must also be resilient enough to allow this opposite spring back motion of its material. Suitable materials include, but are not limited to Ti6Al4V ELI, stainless steel, polymers, absorbable polymers, titanium and any other suitable material. Furthermore, it is contemplated that ring 10 may, in certain sections, be coated with a hard surface layer to ensure proper cooperation with plate 50. For example, in embodiments where plate 50 is also constructed of Ti6Al4V ELI, ring 10 may be coated in certain areas or over its entire surface with TiNbN. This difference in materials preferably creates a difference in hardness level between the two parts, with the coating of ring 10 being harder than the material of plate 10. Thus, ring 10 or its surface may be coated with any material that is harder than that of plate 50. Some other materials, may include titanium and the like. This will be discussed more fully below.

Figure 6:
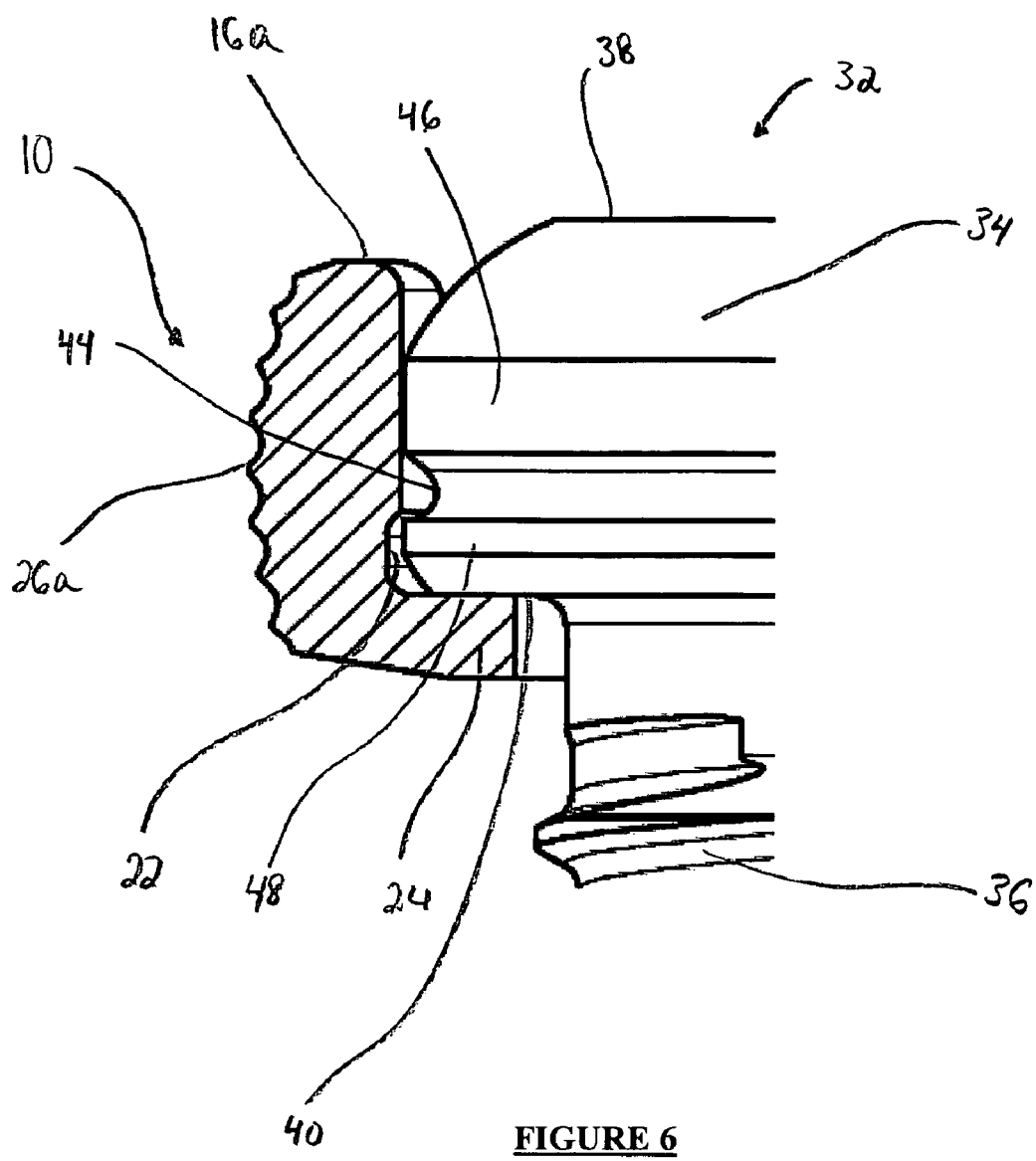
FIG. 6 is a partial cross sectional side view of the polyaxial locking mechanism or ring of FIG. 1, illustrating its engagement with a screw.

FIG. 6 depicts the cooperation between ring 10 and a bone screw 32. Of course, it is to be understood that ring 10 may be utilized in conjunction with other fixation mechanisms, such as threaded or unthreaded rods, pins, or the like. Bone screw 32 as shown includes a head portion 34 and a threaded shank 36. While threaded shank 36 is typical of a standard shank of a bone screw (either self tapping or not), head portion 34 includes several elements tailored towards cooperation with ring 10. First, head portion 34 is sized and configured so that upon insertion of shank 36 through central opening 28 a bottom surface 40 of the head portion engages circumferential wall 24 of body 12. This engagement prevents screw 32 from being completely pushed through central opening 28. A top surface 38 of head portion 34 preferably includes a depression and/or extension 42 (best shown in FIG. 7) capable of engaging an insertion tool, such as a screw driver. Head portion 34 is also provided with an axial groove 44 which essentially divides head portion 34 into a top section 46 and a bottom section 48. Upon the above-discussed constriction of ring 10, bottom section 48 is preferably engaged within interior groove 22 formed in body 12. This engagement or cooperation preferably creates a stronger connection between ring 10 and screw 32 to ensure that they lock rotationally.

FIG. 7 depicts the cooperation among ring 10, screw 32, and bone plate 50. As is discussed above, ring 10 is disposed within a properly sized and shaped aperture 52 formed in plate 50. This may be done prior to a surgical procedure, such that plate 50 is packaged with ring 10 already disposed therein. During an operation, a surgeon or other medical professional first preferably positions plate 50 with respect to a bone surface. This step may involve manipulating two bones or bone fragments with respect to one another. With plate 50 positioned, screw 32 is then inserted through central opening 28. During or subsequent this step, screw 32 may be polyaxially moved, as is allowed by the cooperation of ring 10 and aperture 52. Thus, screw 32 may be positioned about several different axis so as to create the necessary force to hold two bones or bone fragments together, so as to engage a certain portion of the bone surface, and/or for any other reason determined by the surgeon or medical professional.

Once properly positioned, screw 32 may be tightened into the bone surface. It is noted that for self tapping screws, a simple tightening of same may suffice. Otherwise, for other types of screws, a drilling step may be required prior to insertion of the screw in the bone. This drilling step is preferably done prior to introduction of screw 32 within central opening 28, and may or may not involve the use of a drill guide. Upon fully tightening of screw 32 into the bone, bottom surface 40 of head portion 34 engages circumferential wall 24 of body 12 (this position is depicted in FIG. 6). Ring 10 and screw 32 may now be locked with respect to plate 50.

Figure 8:
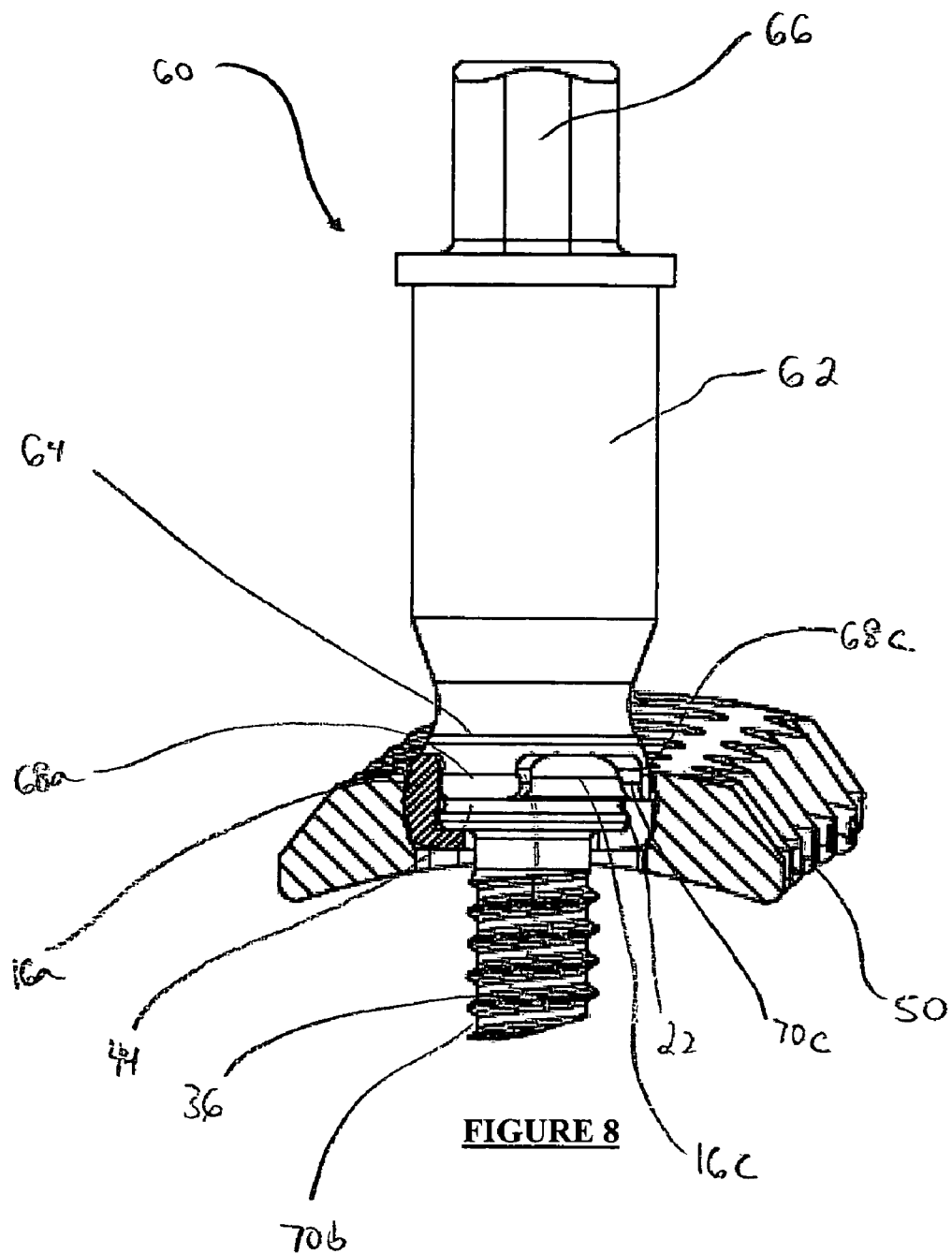
FIG. 8 is a cross sectional perspective view of the polyaxial locking mechanism of FIG. 7 with a ring driver attached thereto.
Figure 9:
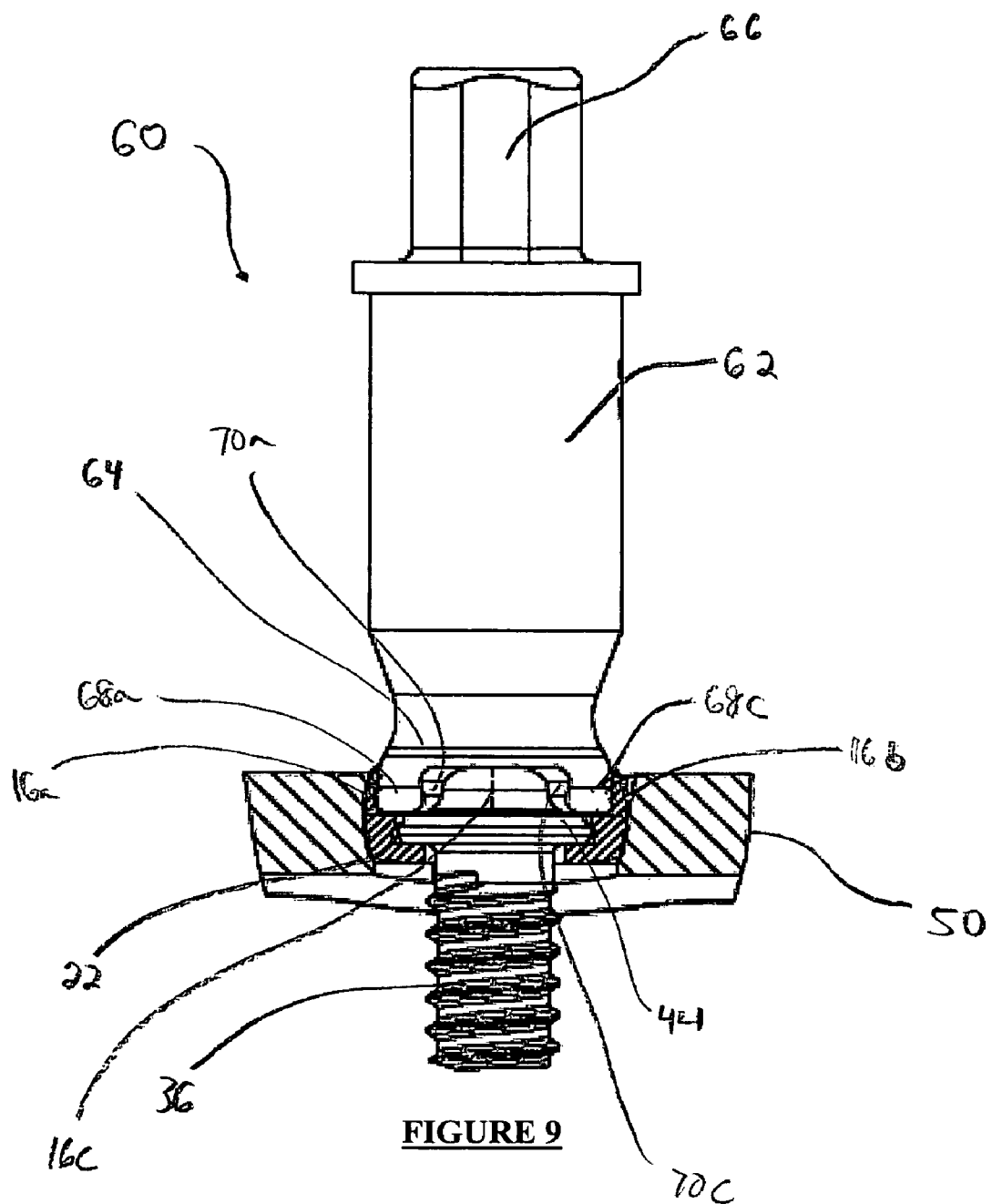
FIG. 9 is a cross sectional side view of the polyaxial locking mechanism of FIG. 7 with a ring driver attached thereto.
Figure 10:
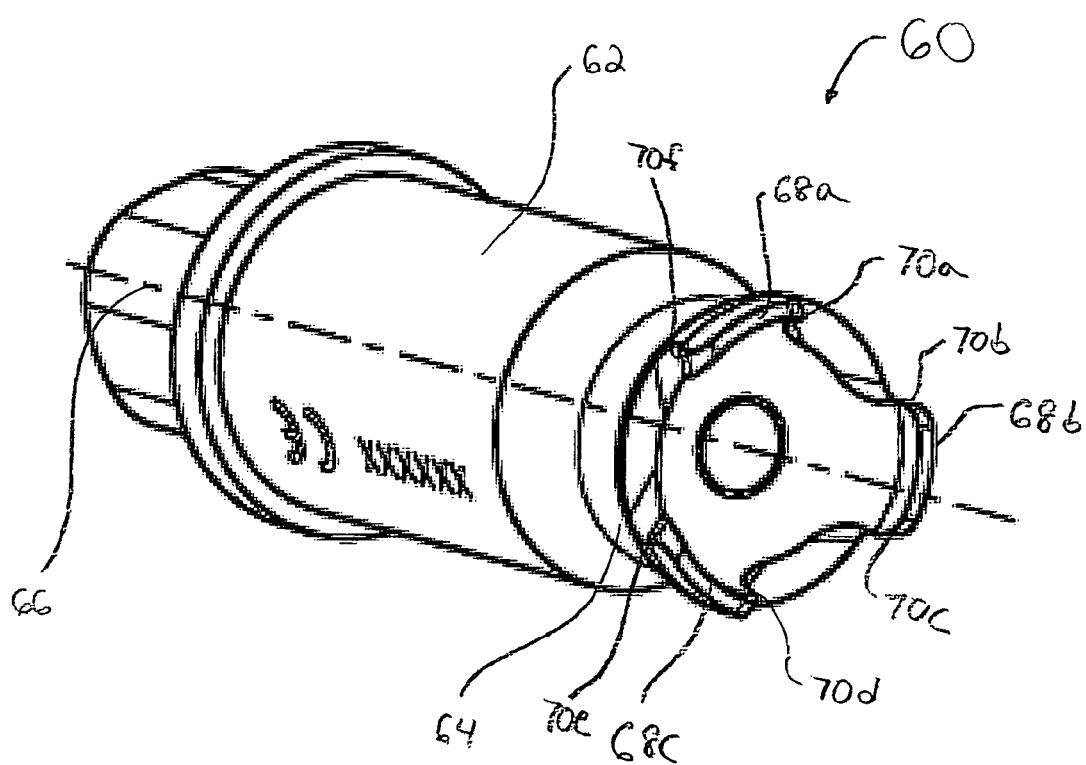
FIG. 10 is a perspective view of the ring driver of FIGS. 8 and 9.

FIGS. 8 and 9 depict the tightening of ring 10 with respect to plate 50, as well as a ring driver 60 utilized in this tightening step. It is to be understood that this tightening step requires the use of ring driver 60 (or another suitable tool) to rotate ring 10 to create the aforementioned constriction and locking. FIG. 10 depicts one suitable ring driver 60 for use with the above-described ring 10 and plate 50. Ring driver 60 preferably includes an elongate portion 62 connected to a driver head 64. It is noted that elongate portion 62 may comprise a handle, or, as is shown in FIGS. 8-10, an end of the portion opposite to head 64 may include an interface 66 for connection to another tool like a manual or motorized handpiece, a drill, or the like. Driver head 64 preferably includes at least one, and preferably three fingers 68a-c sized and shaped so as to be capable of being disposed between peaks 16a-c, within valleys 18a-c. More particularly, fingers 68a-c are preferably sized so that they may easily fit within valleys 18a-c respectively, and preferably include surfaces 70a-f which are essentially mirror images of tapered flanks 30a-f. This ensures a snug fit between the components. It is to be understood that there may exist some play between the structure of fingers 68a-c and peaks 16a-c. Thus, rotation of driver 60 in either direction may first involve a slight movement of fingers 68a-c with respect to ring 10. However, the ultimate snug fit between driver 60 and ring 10 preferably allows for a better grip and fluid force transmission during tightening/loosening of ring 10 with respect to plate 50.

During tightening of ring 10 within aperture 52 of plate 50, the plurality of grooves formed on exterior grooved areas 26a-c preferably cut into the inside surface of aperture 52. This creates a strong, form fit contact. In preferred embodiments, the grooves on areas 26a-c are designed so that different friction forces are exhibited on ring 10 upon tightening. For instance, the friction between ring 10 and plate 50 is increased perpendicular to the grooves formed on exterior grooved areas 26a-c after tightening. This allows for less of a forced to be required for tightening, than for loosening, thereby preventing the unwanted loosening of ring 10 with respect to plate 50. Hence, rotation of ring 10 in one direction is easier than in the other. In addition, the grooves on areas 26a-c may be tapered off so that full polyaxial movement of ring 10 with respect to plate 50 may be allowed when ring 10 is in the loosened position, but, upon tightening, the grooves properly cut into the inside of aperture 52. It is to be understood that the above-described difference in material hardness on certain sections of ring 10 with regard to plate 50 preferably applies to areas 26a-c. In other words, areas 26a-c are preferably coated with a material which exhibits harder properties than that of at least the inside surface of aperture 52. This ensures easy and more solid cutting of ring 10 into plate 50, which in turn provides a more solid locking between the two components.

When ring 10 is fully rotated in the tightening direction, ring 10, screw 32, and plate 50 are all preferably locked with respect to one another. Of course, rotation in the opposite, or loosening direction, back to the original position preferably allows polyaxial movement of ring 10 and screw 32 with respect to plate 50. Thus, if for any reason, the surgeon or medical professional determines that screw 32 has been improperly positioned after tightening, ring 10 may be loosened and the screw may be repositioned. The step may also be performed through the use of driver 60.

The above described improved polyaxial locking mechanism or ring 10 essentially strengthens the locking among ring 10, screw 32, and plate 50. Cut outs 20a and 20b, and tapered flanks 30a-f (and their cooperation with fingers 68a-c of driver 60) preferably make for an easier constriction of the ring, and hence easier tightening of ring 10 with respect to plate 50. The cooperation between interior groove 22 of ring 10 and bottom section 48 of screw 32 preferably ensures that the screw remains within the ring, even upon the application of push-out forces and bending forces caused by rotational movement of screw 32 with respect to plate 50. These forces may be created upon the shifting of plate 50 or the bone surfaces being treated. Additionally, the fact that the grooves of areas 26a-c cut into the interior of aperture 52 creates a solid interface between ring 10 and plate 50 in the tightened position. All of this creates a stronger polyaxial locking between any bone plate employing ring 10 and suitable fixation mechanism, such as a screw, rod or the like.

It is to be understood that the polyaxial locking mechanism of the present invention may take on many different forms. For example, although shown as being a circular ring, it is contemplated to provide a differently shaped structure, such as an oblong structure or a shape including one or more straight sides. In addition, it is to be understood that the present invention may be applied to any known bone plate, with such plate including an aperture or the like suitable for reception of the polyaxial locking mechanism therein. Finally, it is to be understood that in accordance with the present invention, the polyaxial locking mechanism may be designed so as to be retained within an aperture of a bone even without locking between the two. For example, in the above-described embodiment of the present invention, aperture 52 of plate 50 is preferably designed so as to include a curvature which tends to accept and retain ring 10 therein. In such a case, polyaxial movement is still allowed when ring 10 is in the initial position, and prevented upon tightening.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A polyaxial locking mechanism for locking a fixation mechanism with respect to a bone plate comprising:
   a body disposed within an aperture formed in the bone plate, the body including:
   a central opening for receiving the fixation mechanism, the central opening having an uppermost portion and a lowermost portion;
   a slot formed through the body and into the central opening;
   two peaks separated by a valley for use in engagement with a driver for rotating the body, the valley having an upper dimension and a lower dimension extending across the valley, the upper dimension being smaller than the lower dimension for securing the driver within the valley;
a radially inwardly extending circumferential wall; and
a circular interior groove formed on an interior surface of the body,
wherein the interior groove engages a portion formed on the fixation mechanism and the radially inwardly extending circumferential wall prevents the fixation mechanism from being pushed through the lowermost portion of the central opening, and
wherein in a loosened position the body is capable of polyaxial movement with respect to the bone plate, and upon rotation of the body to a tightened position the body, the fixation mechanism, and the bone plate are fixed with respect to one another.

2. The polyaxial locking mechanism of claim 1, wherein the body is a circular ring shape.

3. The polyaxial locking mechanism of claim 1, wherein the body further includes an axially extending cut out formed on the interior surface of the body.

4. The polyaxial locking mechanism of claim 1, wherein the peaks and valley create surfaces complementary to a finger formed on an end of the driver.

5. The polyaxial locking mechanism of claim 1, wherein the fixation mechanism is a screw having a head, and the portion is formed on the head.

6. The polyaxial locking mechanism of claim 1, further comprising an exterior groove formed on an exterior surface of the body.

7. The polyaxial locking mechanism of claim 6, wherein the exterior groove engages an inner surface of the aperture formed in the bone plate upon rotation of the body.

8. The polyaxial locking mechanism of claim 7, wherein the engagement of the exterior groove and the inner surface of the aperture creates a different frictional force for loosening and tightening of the body within the aperture.

9. The polyaxial locking mechanism of claim 7, wherein the exterior groove is tapered.

10. The polyaxial locking mechanism of claim 6, wherein the body includes a plurality of exterior grooves positioned in different sections.

11. The polyaxial locking mechanism of claim 1, wherein the aperture is eccentric or oblong.

12. A bone plate having the polyaxial locking mechanism of claim 1 disposed therein.

13. A polyaxial locking mechanism for locking a bone screw with respect to a bone plate comprising:
a circular ring shaped body disposed within an aperture formed in the bone plate, the body including:
a central opening for receiving the bone screw, the central opening having an uppermost portion and a lowermost portion;
a slot formed through the body and into the central opening;
a radially inwardly extending circumferential wall engaged with the bone screw to prevent the bone screw from being pushed through the lowermost portion of the central opening;
a circular interior groove formed on an interior surface of the body, wherein the interior groove engages a flange formed on a head of the bone screw, a thickness of the circular interior groove being substantially identical to a thickness of the flange, such that the flange interacts with the circular interior groove; and
a plurality of exterior grooves formed on an exterior surface of the body, the exterior grooves being situated in different sections,
wherein in a loosened position the body is capable of polyaxial movement with respect to the bone plate, and upon rotation of the body to a tightened position the body, the bone screw, and the bone plate are fixed with respect to one another.

14. The polyaxial locking mechanism of claim 13, wherein the body further includes an axially extending cut out formed on the interior surface of the body.

15. The polyaxial locking mechanism of claim 13, wherein the body further includes two peaks and a valley for use in engagement with a driver for rotating the body.

16. The polyaxial locking mechanism of claim 15, wherein the peaks and valley create surfaces complementary to a finger formed on an end of the driver.

17. The polyaxial locking mechanism of claim 13, wherein the exterior groove engages an inner surface of the aperture formed in the bone plate upon rotation of the body.

18. The polyaxial locking mechanism of claim 17, wherein the engagement of the exterior groove and the inner surface of the aperture creates a different frictional force for loosening and tightening of the body within the aperture.

19. A bone plate having the polyaxial locking mechanism of claim 13 disposed therein.

20. A polyaxial locking mechanism for locking a bone screw with respect to a bone plate comprising:
a circular ring shaped body disposed within an aperture formed in the bone plate, the body including:
a central opening for receiving the bone screw, the central opening having an uppermost portion and a lowermost portion;
a slot formed through the body and into the central opening;
a circular interior groove formed on an interior surface of the body, the interior groove being adapted to engage a flange formed on the bone screw;
a plurality of exterior grooves formed on an exterior surface of the body, the exterior grooves being situated in different sections;
a cut out formed on the interior surface of the body;
two peaks separated by a valley for use in engagement with a driver for rotating the body, the valley having a lower dimension and an upper dimension extending across the valley, the upper dimension being smaller than the lower dimension, wherein the two peaks extend in an axial direction of the circular ring shaped body and are engagable when the body is disposed within the bone plate, and
a radially inwardly extending circumferential wall engaged with a head portion of the bone screw to prevent the bone screw from being pushed through the lowermost portion of the central opening,
wherein in a loosened position the body is capable of polyaxial movement with respect to the bone plate, and upon rotation of the body to a tightened position the body, the bone screw, and the bone plate are fixed with respect to one another.

21. A fracture fixation system comprising:
a bone plate having a non-circular aperture formed therein;
a body disposed within the aperture, the body including:
a central opening having an uppermost portion and a lowermost portion;
a bone fastener received within the central opening of the body;
a slot formed through the body and into the central opening;
a radially inwardly extending circumferential wall engaged with the bone fastener for preventing the bone fastener from being pushed through the lowermost portion of the central opening; and a circular interior groove formed on an interior surface of the body, the bone fastener having a flange formed on a head of the fastener, a thickness of the circular interior groove being substantially identical to a thickness of the flange, such that the flange interacts with the circular interior groove;

wherein in a loosened position the body is capable of polyaxial movement with respect to the bone plate, and upon rotation of the body to a tightened position the body, the bone fastener, and the bone plate are fixed with respect to one another.

22. The fracture fixation system of claim 21, wherein the body is a circular ring shape.

23. The fracture fixation system of claim 21, wherein the body further includes an axially extending cut out formed on the interior surface of the body.

24. The fracture fixation system of claim 21, wherein the body further includes two peaks and a valley for use in engagement with a driver for rotating the body when the body is disposed within the aperture, wherein the two peaks extend in an axial direction of the body.

25. The fracture fixation system of claim 24, wherein the peaks and valley create surfaces complementary to a finger formed on an end of the driver.

26. The fracture fixation system of claim 21, further comprising an exterior groove formed on an exterior surface of the body.

27. The fracture fixation system of claim 26, wherein the exterior groove engages an inner surface of the aperture formed in the bone plate upon rotation of the body.

28. The fracture fixation system of claim 27, wherein the engagement of the exterior groove and the inner surface of the aperture creates a different frictional force for loosening and tightening of the body within the aperture.

29. The fracture fixation system of claim 26, wherein the exterior groove is tapered.

30. The fracture fixation system of claim 26, wherein the body includes a plurality of exterior grooves positioned in different sections.

* * * * *

UNITED STATES PATENT AND TRADEMARK OFFICE
CERTIFICATE OF CORRECTION

| | | |
|---|---|---|
| PATENT NO. | : 8,287,575 B2 | Page 1 of 1 |
| APPLICATION NO. | : 11/595795 | |
| DATED | : October 16, 2012 | |
| INVENTOR(S) | : Beat Mürner and Philippe Lehmann | |

It is certified that error appears in the above-identified patent and that said Letters Patent is hereby corrected as shown below:

In the Specification

Column 3, line 58, "axis" should read -- axes --.

Signed and Sealed this
Eleventh Day of August, 2015

Michelle K. Lee
*Director of the United States Patent and Trademark Office*